United States Patent [19]

Deal

[11] Patent Number: 5,087,249
[45] Date of Patent: Feb. 11, 1992

[54] SYRINGE CAP HOLDING DEVICE

[76] Inventor: Richard E. Deal, 614 S. Moore, Algona, Iowa 50511

[21] Appl. No.: 570,504

[22] Filed: Aug. 21, 1990

[51] Int. Cl.$^5$ ............................................. A61M 5/32
[52] U.S. Cl. ..................................... 604/192; 604/263
[58] Field of Search ........................ 604/192, 263, 187

[56] References Cited

U.S. PATENT DOCUMENTS

| 86,016 | 1/1869 | Howell . | |
|---|---|---|---|
| 1,023,042 | 4/1912 | Scott . | |
| 2,977,150 | 3/1961 | Thomas | 294/118 |
| 4,596,562 | 6/1986 | Vernon | 604/263 |
| 4,717,386 | 1/1988 | Simmons | 604/192 |
| 4,742,910 | 5/1988 | Staebler | 206/365 |
| 4,795,443 | 1/1989 | Permenter et al. | 604/198 |
| 4,840,272 | 6/1989 | Goldman | 206/365 |
| 4,846,803 | 7/1989 | Emerson | 604/263 |
| 4,955,865 | 9/1990 | Steiner | 604/192 |
| 4,979,945 | 12/1990 | Wade et al. | 604/192 |

FOREIGN PATENT DOCUMENTS

| 103966 | 8/1926 | Austria . | |
|---|---|---|---|
| 295888 | 12/1988 | European Pat. Off. . | |
| 2620341 | 9/1987 | France . | |
| WO8503006 | 1/1985 | PCT Int'l Appl. . | |
| WO8800477 | 6/1987 | PCT Int'l Appl. . | |
| WO8807873 | 4/1988 | PCT Int'l Appl. . | |
| 2202446 | 9/1988 | United Kingdom . | |
| 2205043 | 11/1988 | United Kingdom | 604/263 |

OTHER PUBLICATIONS

"Reduce the Risk of Needle Puncture Wounds", *Comp-Gard*, Easy to Use Effective Inexpensive, Comp Equipment Corporation, 3 sheets, Nov. 11, 1983.

*Primary Examiner*—John D. Yasko

[57] ABSTRACT

A syringe cap holding device is provided which allows a cap to be safely place on a syringe needle without exposing the user's hand or fingers to the needle. The device includes a handle and a head member angularly disposed with respect to the handle. The head member includes a cavity for receiving and releasably engaging the syringe cap. The cavity is defined by a pair of opposed, resilient clips, or alternatively, by a pair of spaced apart walls innerconnected at one end.

16 Claims, 2 Drawing Sheets

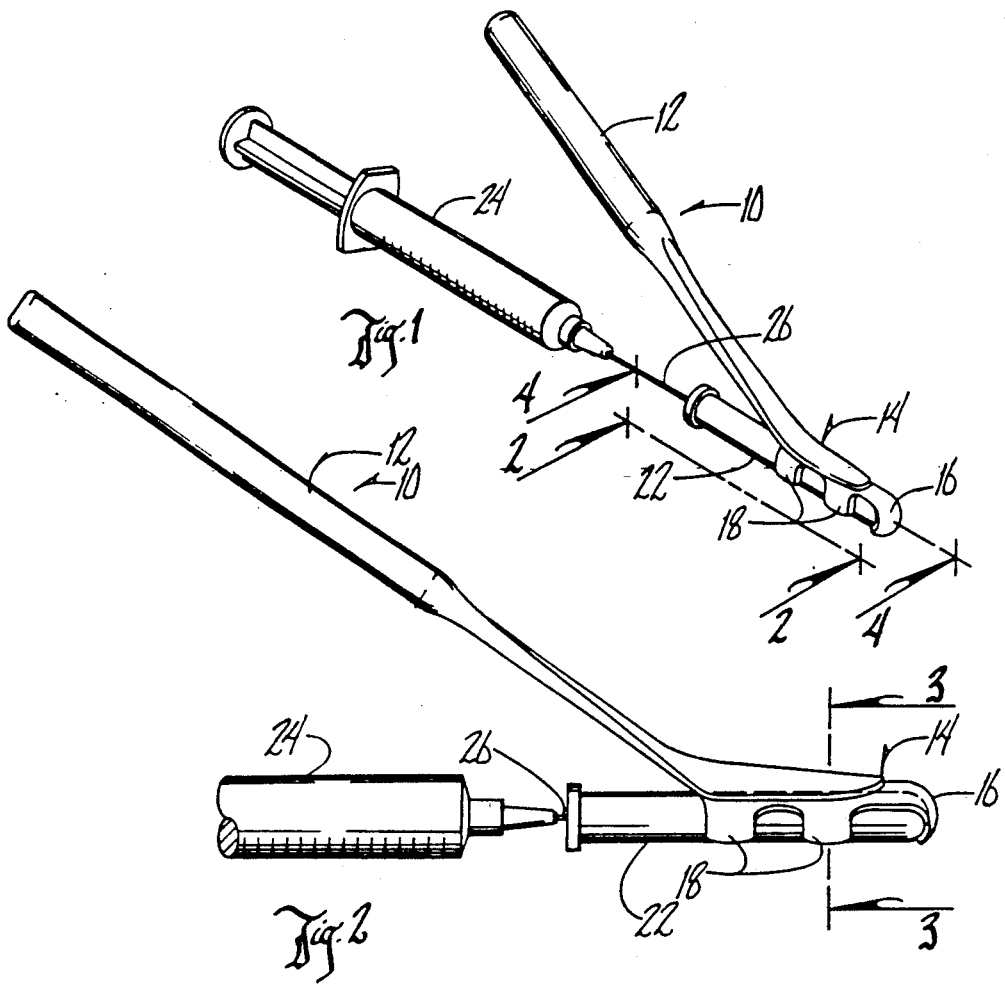
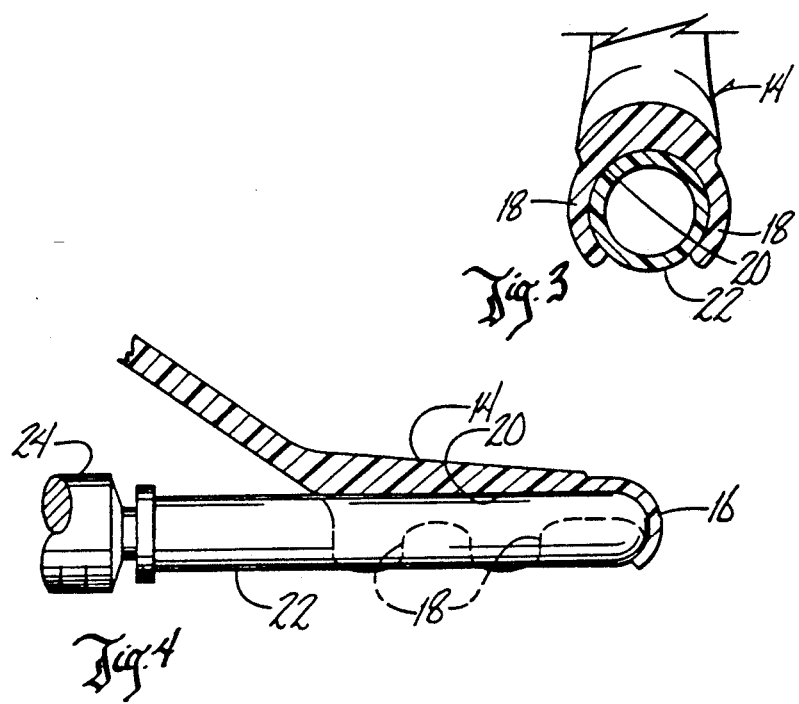

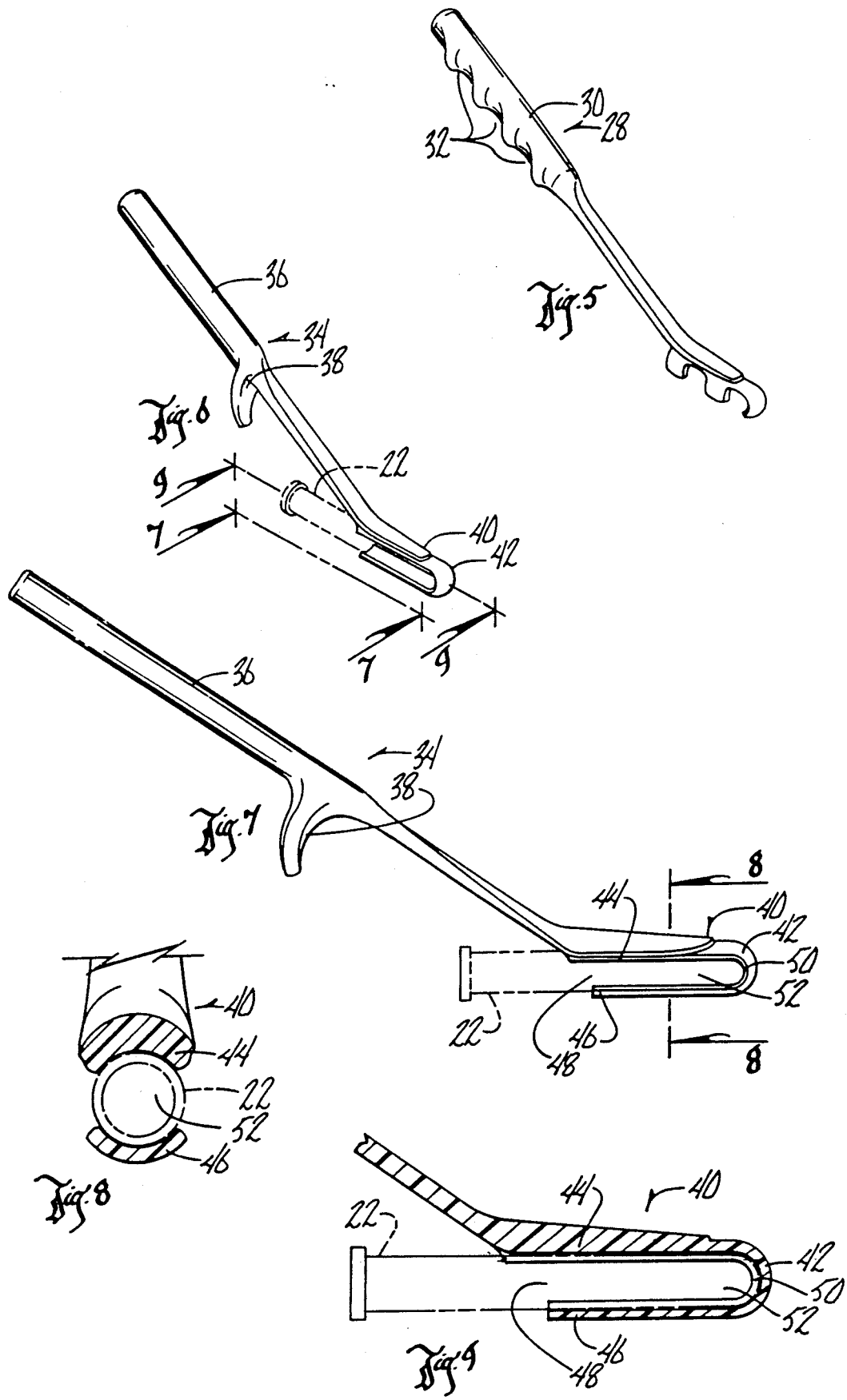

1

SYRINGE CAP HOLDING DEVICE

BACKGROUND OF THE INVENTION

The present invention relates to a device for holding a syringe cap, and in particular, a device to enable the user of a syringe to place the syringe cap on the syringe without exposing the user to the dangers associated with a contaminated syringe needle. The needle of a syringe is a hazard which medical personnel expose themselves to every day. Besides the painful pricks, scratches and cuts, medical personnel who handle syringes are subject to the possibility of contracting viruses and diseases, such as AIDS and hepatitis.

Generally, a syringe cap is placed over the needle to protect the needle from damage prior to use and to prevent injury to those who handle the syringe. In order to place the cap on the needle, the user normally grasps the cap and necessarily exposes his or her fingers to the needle tip.

Therefore, a primary objective of the present invention is the provision of a device for holding a syringe cap in order to allow the user to place a syringe needle within the cap.

Another objective of the present invention is the provision of a syringe cap holder which allows the user to place a syringe cap on a syringe needle without exposing the user to the hazards of a needle prick.

Still another objective of the present invention is the provision of a disposable syringe cap holder which is economical to manufacture and safe and easy to use.

These and other objectives will become apparent from the following description of the invention.

SUMMARY OF THE INVENTION

A syringe cap holder is provided for safely and easily placing the syringe cap on a syringe. The holder comprises a handle and a head member. The head member has opposed resilient clips extending from its sides and a closed terminal end. The resilient clips and the terminal end form an elongated cavity for receiving a syringe cap which is axially introduced.

In use, the syringe cap holder enables the user to place the syringe cap on the syringe without exposing the user to the dangers of a needle prick. The user places the syringe cap within the cavity. The syringe is slid into the cap. Since the user's fingers are located on the handle away from the syringe cap, the user can avoid an accidental needle prick, thereby eliminating the hazards associated with handling a syringe. By pulling the handle and the syringe apart, the resilient clips open so as to allow the syringe to be removed from the syringe cap holder with the syringe cap still on the syringe.

The syringe cap holder also allows a capped syringe to be inserted into the cavity, with the user pinching the resilient clips so as to hold the cap while the syringe is removed from the cap.

The handle and head member may take alternative shapes. For example, the handle may include finger grooves or a trigger grip. The head member may include a bottom wall extending from the terminal end so as to define an axially extending cavity for holding the syringe cap.

BRIEF DESCRIPTION OF THE DRAWINGS

FIG. 1 is a perspective view of the present invention being used in conjunction with a syringe and syringe cap.

FIG. 2 is a side elevation view of the device shown in FIG. 1.

FIG. 3 is a partial sectional view taken along lines 3—3 of FIG. 2.

FIG. 4 is a sectional view taken along lines 4—4 of FIG. 1.

FIG. 5 is a perspective view showing an alternative handle having finger grooves.

FIG. 6 is a perspective view showing another alternative handle having a trigger grip and an alternative head member.

FIG. 7 is a side elevation view of the holding device shown in FIG. 7.

FIG. 8 is a sectional view taken along lines 8—8 of FIG. 7.

FIG. 9 is a partial sectional view taken along lines 9—9 of FIG. 6.

DESCRIPTION OF THE PREFERRED EMBODIMENT

Referring to the drawings, the syringe cap holder of the present invention is generally designated by the reference numeral 10. The syringe cap holder 10 is comprised of a handle 12 and a head member 14. The longitudinal axes of handle 12 and head member 14 are angularly disposed with respect to one another. The head member 14 has a closed terminal end 16. Opposing pairs of resilient clips 18 extend from the sides of the head member 14.

The resilient clips 18 define a C-shaped cavity 20 with a closed end formed by end 16 of device 10. The C-shaped cavity 20 is elongated so as to axially receive and securely hold a syringe cap 22. A syringe 24 may then be safely inserted into the syringe cap 22 while the user grasps handle 12. Thus, the user's hand and fingers are remote from the cap 22 when the syringe needle is inserted into the cap. Accordingly, the user is less likely to be pricked or scratched by the needle. The closed end 16 prevents the cap from being pushed axially by the syringe needle out of securement by clips 18.

To remove the syringe 20 with the syringe cap 12 still on the needle 26, the user pulls the handle 12 away from the syringe cap 22 in order to spread the resilient clips 18. When the resilient clips 18 are spread, the syringe cap 22 is released. The resilient clips 18 then return to their normal shape. The syringe cap holder 10 may then be used again.

The holder 10 also allows the user to place a capped syringe into the cavity 20, and then pinch the clips 18 so as to hold the cap while the syringe is removed from the cap. The cap is thus positioned in the holder 10 for re-capping the syringe, as described above.

Alternate embodiments of the syringe cap holder are shown in FIGS. 5-9. In FIG. 5, a syringe cap holding device 28 is shown having a handle 30 with finger grooves 32. In FIG. 6, a syringe cap holding device 34 is shown with a handle 36 having a trigger grip 38. It is understood that the handle of the holding device can be modified so as to have any shape which is comfortable to the user. Also, the angle between the handle and the head member may vary, depending on the shape of the handle and other design considerations.

An alternative head member 40 is shown in FIGS. 6-9. Head member 40 includes a continuous loop 42 having opposite walls 44, 46, which are curved in cross section, as seen in FIG. 8. Head member 40 is open at one end 48 and closed at the opposite end 50. The sides of head member 40 between walls 44, 46 are also open. Walls 44, 46 define an elongated cavity 52 for axially receiving the syringe cap 22.

In use, the syringe cap 22 is axially inserted into cavity 52 of head member 40 for retentive engagement by walls 44, 46. Syringe needle 26 can then be inserted into syringe cap 22 until the cap snap fits onto the syringe in its normal manner. Closed end 50 of head member 40 prevents the syringe cap from being pushed out of head member 40 by the syringe 24. After the syringe cap is snap fit onto the syringe, the syringe and connected cap can be axially withdrawn from cavity 52. Thus, the operator's hands and fingers are remotely positioned from head member 40 and syringe cap 22 when the syringe needle 26 is being capped.

It is understood that modifications can be made to the syringe cap holding devices described above without departing from the scope of the present invention. For example, head members 14 and 40 may be used with any of handles 12, 30 or 36. Also, the handle may extend away from the open end or closed end of the head member.

From the foregoing, it is seen that the present invention accomplishes at least all of the stated objectives.

What is claimed is:

1. A hand-held syringe cap holding device, comprising:
    a handle;
    a head member integrally connected to the handle and having at least one pair of opposed, resilient clips extending therefrom, and having a closed terminal end, whereby a syringe cap is releasably held within the head member by the clips; and
    the handle extending angularly from the head member such that a user's hand is remote from the head member.

2. The syringe cap holding device of claim 1 wherein the handle includes a plurality of finger grooves.

3. The syringe cap holding device of claim 1 wherein the handle includes a trigger grip.

4. A hand held syringe cap holding device, comprising:
    a handle;
    a head member integrally formed with the handle and having opposite sides;
    opposed, resilient clips extending from the sides of the head member;
    a closed end on the head member opposite the handle; and
    the clips and the closed end defining a C-shaped cavity for receipt of a syringe cap.

5. The syringe cap holding device of claim 4 wherein the handle extends away from the head member so as to keep the user's hands away from the head member.

6. The syringe cap holding device of claim 4 wherein the clips releasably engage the syringe cap.

7. The syringe cap holding device of claim 6 wherein the syringe cap is removed from the cavity by placing a syringe in the syringe cap and lifting the handle, whereby the opposed clips spread apart so as to release the syringe cap.

8. A method of capping a syringe needle using a cap holding device having a handle, an elongated head member integrally connected to the handle with opposed resilient caps defining an axially extending channel, the method comprising:
    axially inserting the cap into the channel for engagement by the clips;
    holding the device in one hand;
    with the other hand, axially introducing the syringe needle into the cap; and
    moving the syringe needle and cap away from the handle so as to spread the clips apart from one another such that the cap is released from engagement by the clips.

9. A hand-held syringe cap holding device, comprising:
    a handle; and
    a head member integrally connected to the handle and having a pair of spaced apart walls connected at one end opposite the handle so as to define an elongated cavity remote from the handle for holding a syringe cap.

10. The syringe cap holding device of claim 9 wherein the handle extends angularly from the head member such that a user's hand is remote from the head member.

11. The syringe cap holding device of claim 9 wherein the syringe cap is axially inserted and withdrawn from the cavity of the head member.

12. The device of claim 1 wherein the handle includes an elongated substantially cylindrical portion.

13. A hand-held syringe cap holding device, comprising:
    a handle;
    a head member integrally connected to the handle and having at least one pair of opposed, resilient clips extending therefrom, and having a closed terminal end, whereby a syringe cap is releasably held within the head member by the clips; and
    the head member having opposite sides, and the clips extending from the sides of the head member to define a C-shaped cavity.

14. The syringe cap holding device of claim 13 wherein the cavity is elongated so as to axially receive a syringe cap.

15. The syringe cap holding device of claim 14 wherein the syringe cap is removed from the cavity by inserting a syringe needle into the syringe cap and lifting the handle, whereby the opposed clips spread so as to release the syringe cap.

16. A hand-held syringe cap holding device, comprising:
    a handle;
    a head member integrally connected to the handle and having at least one pair of opposed, resilient clips extending therefrom, and having a closed terminal end, whereby a syringe cap is releasably held within the head member by the clips; and
    the handle and head each having a longitudinal axis which intersect one another at an oblique angle.

* * * * *